US005643740A

United States Patent [19]
Billing et al.

[11] Patent Number: 5,643,740
[45] Date of Patent: *Jul. 1, 1997

[54] MONOCLONAL ANTIBODY SPECIFIC FOR ACTIVATED LYMPHOCYTES AND MONOCYTES

[75] Inventors: Ronald J. Billing, 682 Ora Avo Dr., Vista, Calif. 92084; Paul I. Terasaki, Los Angeles, Calif.

[73] Assignee: Ronald J. Billing, Vista, Calif.

[ * ] Notice: The terminal 28 months of this patent has been disclaimed.

[21] Appl. No.: 941,973

[22] Filed: Sep. 8, 1992

Related U.S. Application Data

[63] Continuation of Ser. No. 115,739, Oct. 8, 1987, abandoned, which is a continuation-in-part of Ser. No. 846,828, Mar. 31, 1986, abandoned, which is a continuation of Ser. No. 469,608, Feb. 24, 1983, abandoned.

[51] Int. Cl.$^6$ ............................ C07K 16/22; C07K 16/30
[52] U.S. Cl. ................ 435/7.23; 435/7.24; 530/388.24; 530/388.73; 530/388.75; 530/388.8; 530/388.85
[58] Field of Search ........................ 424/85.8, 85.91, 424/145.1, 153.1, 156.1; 530/388.24, 388.73, 388.75, 388.8, 388.85; 435/7.23, 7.24

[56] References Cited

U.S. PATENT DOCUMENTS 5,045,451  9/1991  Uhr et al. ........................... 435/7.23

FOREIGN PATENT DOCUMENTS 0117705  5/1984  European Pat. Off. .

OTHER PUBLICATIONS

J. Schlom, In S. Broder (ED.), *Molecular and Cellular Research for Future Diagnosis and therapy*, Williams and Wilkins, Baltimore, 1990. pp. 95–134.
R.J. Billing et al, *Hybridoma*, 1, 303–311, 1982.
S. Chatterjee et al, *Hybridoma*, 1, 369–377, 1982.
H. Takahashi et al, *Lancet*, 1155–1157, 19 Nov. 1983.

*Primary Examiner*—David Saunders

[57] ABSTRACT

Hybrid cell line producing monoclonal antibodies reactive with human activated lymphocytes, monocytes and cancer cells directed against a growth factor of approximately 15,000 daltons. Diagnostic and therapeutic uses of the antibody and antigen in cancer, autoimmune disease and transplant rejection are discussed.

1 Claim, 7 Drawing Sheets
(3 of 7 Drawing(s) in Color)

MONOCLONAL ANTIBODY SPECIFIC FOR ACTIVATED LYMPHOCYTES AND MONOCYTES

CROSS-REFERENCE TO RELATED APPLICATION

The present application is a continuation of application Ser. No. 07/115,739 filed on Oct. 8, 1987 and now abandoned, which is a continuation-in-part of application Ser. No. 06/846,828 filed on Mar. 31, 1986 and now abandoned, which is a continuation of application Ser. No. 06/469,608 filed on Feb. 24, 1983 and now abandoned.

BACKGROUND OF THE INVENTION

At the present time the general treatment of organ transplant rejection is accomplished with the use of medications such as azothioprine, prednisone and cyclosporine. The lack of specificity of these drugs produces side effects that limits their dose and thus their effectiveness in immunosuppression. Treatment with the newest drug cyclosporine is expensive, costing several dollars per day and must be taken for the lifetime of the patient. Some patients cannot afford this financial burden and in addition cyclosporine can damage kidneys. Survival of kidney grafts from unrelated donors after one year is approximately 50% and acute rejections that are resistant to drug treatment invariably fall, P. J. Morris (1985) Transplant Proceedings Vol XVII No 1 p 1153. Immunological rejection is still the main cause of loss of transplanted organs, and better treatments are needed.

The current invention is a monoclonal antibody (MA) that has been shown to very effectively reverse kidney graft and corneal graft rejections without adverse side effects. It represents a new approach to the treatment of transplantation rejection in general. It offers new hope to many patients who need transplants of hearts, lungs, liver, bone marrow and other organs without fear of dying from rejection. MAs have been claimed to hold much promise as new antirejection agents (P J Morris, supra), MAs are secreted from hybrid cells called hybridomas. The hybrid cells are made by fusing spleen cells from immunised normal mice and cancer cells called myelomas from the same species. The mice are immunised with cells that express the antigan that one desires a monoclonal antibody (MA) against. Following the fusion hybridomas are selected for those that secrete antibodies against desirable antigens. The hybridoma inherits the normal cell's ability to manufacture antibodies and the cancer cell's capacity to divide. This produces a cell line grown in culture that continuously secretes an unlimited supply of homogeneous antibodies. Therefore mass production of the antibody is a feature suitable for therapeutic uses. The antigenic determinant against which the MA reacts determines the potential value of the hybridoma and the MA. The subject MA (CBL1) reacts with a unique antigen which is found almost entirely on actively dividing cells such as stimulated lymphocytes (called blast cells) and cancer cells of all types. The antigan is located on the cell membrane and controls the growth and division of these cells.

The subject MA antibody (CBL1) has potential in the treatment of transplant rejection because of its specific toxicity against the cells that are actually causing the rejection of the grafts, i.e. a small percentage of activated lymphocytes. Other monoclonal antibodies such as OKT3 have been used for reversing transplant rejection but the results are disappointing. Cosimi et al (1981) New Engl J. Med 305. The OKT3 MA reacts with all T lymphocytes in the body not just those few that are actively involved in the rejection of the graft. This results in side effects and lack of prolonged effectiveness very similar to side effects seen by drug therapy. Most of the lymphocytes in the body are not dividing and not involved in graft rejection. More effective antirejection and anticancer agents will be specific for dividing cells.

Chemotherapy for cancer has improved survival in some cancers such as childhood leukemia but the survival rate for advanced (metastatic) solid tumors has not dramatically increased in over 30 years. When cancer cells are detected in tissues distant from the primary site then the outcome is usually fatal.

The National Institute of Health recognises these problems and has advocated a serious investigation into newer treatments. Among the most hopeful are monoclonal antibodies and growth factors that will have fewer side effects.

Clinical trials with tumor associated antibodies have been described but thus far with limited success. (Cancer, Devita et al. 1985 Cancer, Lippincott Company, Philadelphia, p 133 and 2244). Although MA directed against tumor antigens provide optimism for adjuvant cancer therapy the lack of specificity of MA tried thus far has limited their effectiveness. Growth factors have not yet been described in clinical trials.

The antigenic determinant of CBL1 appears to be a specific type of tumor related growth factor. Growth factor is a general term for molecules that stimulate and control the growth of cells mainly by binding initially to the cell membrane. Most cells in the body are in a slow growth or non dividing state. The majority of peripheral blood lymphocytes are not dividing unless they are activated by foreign antigens. Cancer cells are rapidly dividing cells of uncontrolled growth. Growth factor binds to the cell membrane and allows nutrients to enter the cell which promote these changes in growth characteristics. (Cancer, Devita et al. 1985, p 50 supra).

Cells growing in cultured nutrient medium require serum as a source of growth factors, (Gospodarowit Det al. Ann. Rev. Biochem. 451, 531 1976). Several of these serum growth factors have now been identified and purified; some are hormones such as insulin, erythropoietin and others are polypeptides that promote growth of certain normal tissue cells such as fibroblast growth factor, epidermal growth factor, nerve growth factor, platelet derived growth factor, transferrin. Interleukin 2 is a growth factor for activated normal T lymphocytes. Autocrine growth factors are produced by cancer cells themselves possibly from viral DNA integrated into the cell genetic material. They are shed into the cellular environment such as culture medium and cause further growth and cell division. (Cancer, Edited by V. T. Devita et al. 1985 p50 supra).

A monoclonal antibody Tac has been reported (Uchiyama et al. J. Immunol. 1981, 126 1393–1397). It appears to react with the interleukin 2 receptor present on activated T lymphocytes but not present on the majority of leukemia cells. However CBL1 has a different antigenic specificity to the Tac antibody. CBL1 reacts with leukemia cell lines but Tac does not. The molecular weight of the CBL1 antigenic determinant is 15,000 daltons. This in addition to its reactivity pattern distinguishes it from other MAs described against activated lymphocytes. MAs that react with growth factors that control the growth of lymphoid cells and cancer cells have not been described. CBL1 can be distinguished by the molecular weight and tissue distribution of the antigenic determinant from the following MAs which react with activated lymphocytes. None of these antibodies has yet been described as a useful therapeutic agent. Omary et el. (1980) *Nature* 286 888–891 (B3-25 cell line); Haynes et al. (1981) *J. Immunol.* 127: 347–351 (5E9 cell line); and Reinherz et al. (1980) PNAS 77: 1581–1592 (OKT9 cell line). A polyclonal rabbit antiserum designated 157 which is specific for blast cells and peripheral blood monocytes has been developed. Billing et al. (1979) *Clin. Immunol. Immunopathol.* 13: 435–443. All of the MAs, 157, B3-25, 5E9 and OKT9 react with the transferrin receptor of 180,000 daltons consisting of two equal protein chains of 90,000 daltons. 4F2 (Haynes et al. 1981 *J. Immunol.* 126, 1409–1414) reacts with an antigan of 120,000 daltons which consists of polypepetides of 40KD and 80KD and is resistant to proteolysis. The CBL1 antigan is a 15K dalton molecule which is not resistant to proteolysis.

SUMMARY OF THE INVENTION

The subject invention is a mouse hybridoma (CBL1) which is capable of producing a novel MA that reacts with an antigen found on essentially all human cancer cells and activated lymphocytes. The MA does not react with the majority of normal tissue and blood cells. The nature and functions of the antigen determine the value and uniqueness of the MA and determine its medical uses. The determinant antigen is approximately 15,000 daltons and is located both on the cell membrane and in the cytoplasm of positive cells. The antigen has the properties of an autocrine growth factor. It is secreted into the culture media by cancer cells and stimulates the growth of cancer cells in general. By binding to the antigenic determinant The MA, CBL1 will prevent the growth of the tumor cells in culture. The mechanism for this inhibition of growth appears to be that the MA neutralises the antigenic determinant and thus inhibits its role of stimulating cell growth when bound to a receptor molecule on the cell surface. The CBL1 antigen can be purified from culture media and shown to increase the growth rate of cultured tumor cells. This increase in growth rate can be inhibited by addition of the CBL1MA to the culture media.

The CBL1 antigen termed hereafter CAGF (cancer associated growth factor) is found in the cytoplasm of normal lymphocytes in the blood but not on the surface membrane of these cells. Following stimulation of normal lymphocytes with the mitogen, phytohemaglutinin (PHA), the CAGF antigen migrates within a few hours to the cell membrane. PHA stimulated cells are called activated or blast cells and unlike the majority of lymphocytes they proceed to make DNA and divide after 3 or 4 days. This indicates that CAGF is functioning at the cell membrane to control cell growth in some yet unknown way. CBL1 will bind to the membrane of activated lymphocytes but not to the membrane of normal unstimulated lymphocytes in the blood of healthy donors.

When lymphocytes from two unrelated donors are mixed in tissue culture medium a reaction occurs called the mixed lymphocyte reaction (MLR). In MLR unstimulated lymphocytes begin to become blast cells and express CAGF on their surface membrane, As in the use of PHA activated cells, CBL1 will bind to the cell membranes of MLR activated cells but not to the membranes of normal lymphocytes.

These tests done outside the body i.e. in vitro relate to the observed therapeutic uses of the CBL1 MA. The MLR test is an in vitro model of what is happening in a human transplant situation. The recipient of the transplanted organ reacts to the foreign graft by producing activated lymphocytes that attack the graft causing rejection of the transplanted organ. CBL1 will dramatically reverse transplant rejection without side effects to the patient. The most probable explanation is that the MA specifically destroys the activated lymphocytes that are mainly responsible for the rejection process but does not kill normal cells. This includes normal white blood cells which are needed to protect the patient against infections.

PHA stimulation of lymphocytes in vitro is a model of what happens in the body during allergic reactions and autoimmune diseases. In these diseases activated lymphocytes are produced in response to a foreign allergen. In the case of autoimmune diseases the body reacts to a molecule that is a functional part of the body itself. For example in rheumatoid arthritis the patient makes antibodies to his own immunoglobulin molecules, in multiple sclerosis there is an autoimmune attack against parts of the nervous system and in systemic lupus antibodies are made against DNA. Activated lymphocytes are thought to be involved as an important mediator of the immune disease process. Cell membrane binding tests have shown that patients with these diseases have a significant increase in CBL1 positive cells. Therefore by killing these activated cells the CBL1 may have therapeutic applications in patients with these disorders.

Unlike MAs described in prior art CBL1 has no side effects on patients or on nonhuman primates (Rhesus monkeys) treated. Therefore CBL1 can be used as a safe therapeutic agent to treat transplant rejection, autoimmune diseases or cancer. The reason for the lack of side effects appears to be that CBL1 will only kill those cells that express the CBL1 antigen (CAGF) on the cell surface membrane and these cells are restricted essentially to activated lymphocytes and tumor cells. The normal cells in blood and body tissues are essentially negative. Therefore the antibody will attack mainly those cells that are causing the disease leaving normal cells unaffected.

The CBL1 MA kills cells by binding to the specific antigen CAGF present on the cell surface. Serum complement factors react with the MA bound to antigen on the cell surface to lyse the cell. This is termed complement dependent cell cytotoxicity. B lymphocytes can also be used to kill cells to which MA is bound. Cells with antigen in the cytoplasm but not on the cell surface would not be killed.

The MA CBL1 has been used both intravenously (iv) and intramuscularly (im) to treat over 30 patients and no side effects were observed. The CBL1 MA was first used to prolong skin transplants in Rhesus monkeys. There was a significant increase in graft survival without any observable reactions against normal body cells. Because of the safety of the MA in the animal studies, CBL1 has been used in several clinical trials. It reversed acute kidney transplant rejection in 17 of 19 patients who had failed conventional drug therapy. In another study corneal graft rejections were reversed in six patients who had very poor or no vision. Unlike reagents described in prior art there were no significant side effects observed and the reversal of graft rejection appeared to be permanent.

The subject hybridomas and monoclonal antibodies can be obtained substantially following the well-known procedure of Kohler and Milsrein, *Eur. J. Immunol.* (1976) 6:511–591. The method involves hyperimmunisation of a mammalian host,e,g., a mouse, with a tumor cell line (CEM). Shortly after the last immunisation, the host spleen is removed and the spleen cells fused with myeloma cells to produce hybridomas having a range of specificities. The hybridomas are selected on HAT media, and the supernatants screened for antibodies having the desired specificity.

Those colonies which produce the desired antibodies may then be cloned by limiting dilution and grown out in flasks. Production of the desired antibodies may be enhanced by intraperitoneal injection of the hybridoma into a mammalian host to produce high-titered ascites fluid. In contrast to antisera derived directly from an immunised host, the monoclonal antibodies of the present invention are substantially free from immunoglobulins having differing specificities.

The antibodies of the subject invention can be used to isolate the antigenic determinant by the method of affinity chromatography, (see booklet, "Affinity Chromatography" by Pharmacia Fine Chemicals, Uppsala, Sweden). Essentially the antibody is bound covalently to Sepharose$^R$ beads to prepare an immunosorbent column. By lysing the CEM cells, separating the cellular debris, and then passing the supernatant through the column, the molecules displaying the determinant will bind to the column. After washing the column to remove nonspecifically bound proteins, the antigan or determinant may be eluted, using detergents, urea, etc. in programmed gradient elution. The antigan may then be isolated and used to hyperimmunise an appropriate host followed by fusion of splenocytes with a fusion partner and screening for the desired hybridoma(s). In this way, monoclonal antibodies having substantially identical specificities, but which differ in class, such as IgM, IgG, IgA, IgE and IgD, may be obtained. In addition, antibodies from a variety of different hosts can be obtained. The purified antigen can also be used for diagnostic and therapeutic procedures and as a growth factor to stimulate cell growth.

The subject antibodies can be used directly as therapeutic agents. For such use, it is desirable to employ antibodies of class IgM, IgG2a, IgG2b, or IgG3 which activate the host's own complement system to reduce the population of activated lymphocytes or cancer cells. Alternatively, antibodies of any class may be coupled to cytotoxic agents to provide a composition lethal to target cells but nonlethal to the remainder of the normal peripheral blood population. Suitable cytotoxic agents include chlorambucil (Ghose et al. (1975), Cancer 36:1646–1657), whole diptheria toxin (Moolten et al.(1972) J.

Natl. Cancer Inst. 49:1059–1062; Moolten et al. ibid 55:473–477; and Thorpe et al. (1978) Nature 271:752–755), and the A chain of ricin toxin (Oeltmann et al. (1979) J. Biol. Chem. 254:1022–1027; and Oeltmann et al., ibid, 254:1028–1032). For administration to a patient, the antibodies are dissolved in physiologically acceptable media, such as saline, or phosphate buffered saline and administered in a variety of ways, conveniently intravenously or intramuscularly.

The subject antibodies will also find use in detection of malignant cells and in immunological classification of leukemia. Leukemias can be divided into immunological subsets depending on the particular surface antigens displayed by the malignant cells. For example, CBL1 antibody is reactive with three out of the four generally recognised morphological types of leukemia, being nonreactive with chronic lymphocytic leukemia (CLL). CBL1 would thus be useful, in combination with other antibodies having different specificities, in clinical diagnosis of a patient having leukemia. Malignant lymphocyte cells which are incapable of reacting with CBL1 would be presumed to be CLL.

A further use of the invention is to detect cancer cells in body tissues by binding of the antibody or antigen coupled to a detection system. A detection system could be a radioactive molecule such as $I^{125}$ covalently bound to the antibody or antigen. The latter complex would specifically bind to the cancer cell following infusion of the radioactively labelled antibody or antigen into the blood. Complex bound to cancer cells could then be detected by X-rays or radioimaging instruments or gamma ray counting. Another detection system would be an enzyme such as peroxidase that could detect antibody bound to cancer cells in tissue sections by changes in the color of a substrate dye. This would be useful in detecting cancer cells in biopsy material.

The CBL1 antigenic determinant has medical uses because as an autocrine growth factor it binds to tumor cell membranes. Therefore it can be linked to toxins such as ricin, (and others described above), and used as an anti-tissue rejection or cancer reagent in the same manner as an antibody.

Figure 1:
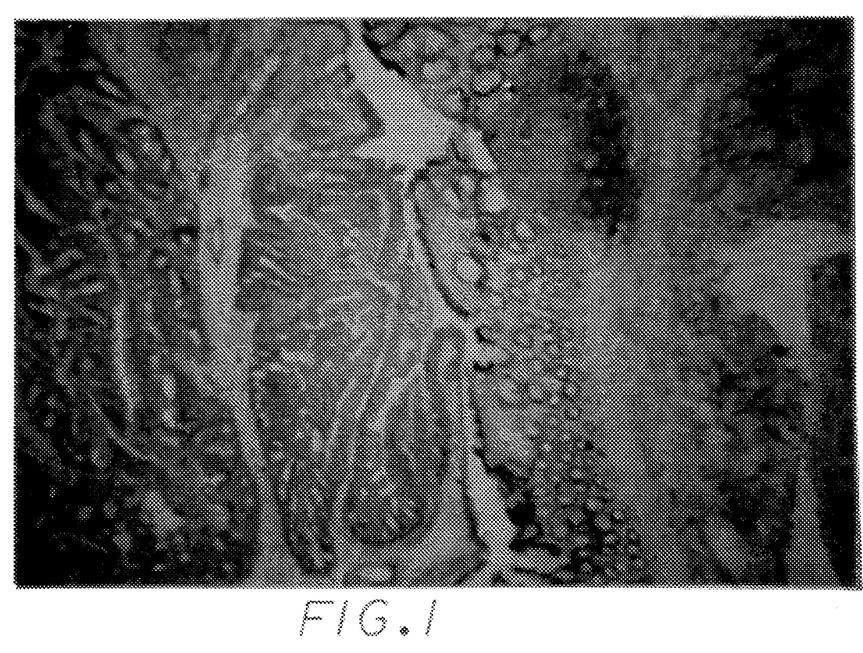
FIGS. 1–4 shows photographs of staining of tissue sections with CBL1.

The CBL1 antibody binds a different epitope to the one that binds the CAGF antigen, i.e. growth factor, to the cell membrane. The CBL1 antibody binds to the epitope of the growth factor that protrudes from the cell membrane and therefore the antibody can bind to the cell surface by means of the antigenic epitope of the growth factor that protrudes from the cell membrane. Another part or epitope of the growth factor binds to the cell membrane. Cells that are not dividing will not have the membrane receptors to bind the CBL1 growth factor and therefore will not bind the CBL1 antigen or antibody. (FIG. 1).

A further use for the invention is the treatment of cancer by infusion of the antibody. It can bind to and kill tumor cells directly by complement dependent cytotoxicity or by binding to the antigen and killing the tumor cell indirectly by depriving it of an essential growth factor.

Autoimmune diseases and allergic reactions are those in which the patient's own immune system produces an immune response against his own tissues or foreign allergens. These reactions can be mediated by activated lymphocytes and therefore may be treatable with antibodies specific for these cells.

The subject hybridoma was deposited on February 24th 1983 at the ATCC, American Type Culture Collection, 12401 Parklawn Dr., Rockville, Md. 20852 and was given the ATCC number HB 8214.

DETAILED DESCRIPTION OF THE INVENTION

Method of production of the Hybridoma and Monoclonal Antibody

Two 6 week old female Balb/c mice (Simonsen Labs) were immunised intravenously with $2 \times 10^6$ acute leukemia cells weekly for 3 weeks. Three days after the final injection the spleens were removed sterilely into RPMI medium and a single cell suspension of splenocytes made by teasing the tissue in RPMI medium with a scalpel. $2 \times 10^8$ spleen cells were fused with $50 \times 10^6$ P3×63 Ag8 651 myeloma cells (from ATCC) in 50% polyethylene glycol 4000 in RPMI medium. The fused cells were plated in six microtest plates containing 96 wells and allowed to grow in RPMI medium with 20% fetal calf serum containing hypoxanthine, aminopterine and thymidine. After three weeks, hybridoma colonies had grown out and supernatants from the microtest plate wells were screened by microcytotoxicity against the immunising cell and normal lymphocytes. One microtest plate from 600 produced a supernatant from a hybridoma that showed reactivity against tumor cells but not normal cells. This hybridoma was cloned by the limiting dilution method, expanded and frozen in liquid nitrogen. Other cloned cells were grown to produce ascites fluid in the peritoneal cavity of pristane primed Balb/c mice. 20×10⁶ cells per mouse produced 4–6 ml ascitic fluid containing high levels of monoclonal antibody. The fusion and purification techniques are described in detail in Monoclonal Antibodies, 1980 ED by R. H. Kennet et al. PLenum Press, New York. The antibody was purified by ammonium sulfate (40%) precipitation followed by exclusion gel filtration on S300 (Sephadex$^R$). Materials used in characterisation of CBL1.

Leukemia Cells:

Heparinised peripheral blood samples were drawn from children and adults with active leukemia. The acute lymphocytic leukemia (ALL,) end acute myelocytic leukemia (AML) patients had peripheral blood blast counts greater than 90%. Leukemia cells from patients and peripheral blood lymphocytes from healthy donors were isolated by Ficoll-Hypaque$^R$ density gradient centrifugation. Leukemia cells were stored in liquid nitrogen.

Cell lines were grown in suspension cultures in RPMI 1640 containing 10% heat-inactivated fetal calf serum. Most were obtained from ATCC, Rockville, Md.

T and B lymphocytes:

T and B lymphocytes were prepared from whole lymphocytes by the nylon-wool method. Danilovs et al. (1980) *Histocompatibility Testing* 1980, Terasaki (ed.) UCLA Tissue Typing Laboratory, Los Angeles, Calif., pp. 287–288.

PHA Blasts:

Whole peripheral blood lymphocytes isolated by the Ficoll-Hypaque$^R$ technique were cultured at 2.5×10⁶ in media 199 (M199) with 20% human AB serum (heat inactivated) at 37° C. with 50 ug/ml of Difco PHA under sterile conditions for 3–6 days. Control lymphocytes were incubated in M199 with 20% human AB serum without PHA. At the end of the culture period, cells were removed , washed and tested by microcytotoxicity against the blast sera.

Monocytes:

Monocytes were isolated using a Percoll$^R$ density gradient. Gutierrez et al. (1979) Immunol. Meth. 29: 57–63. Briefly, the thrombin pellet from lymphocyte isolation containing monocytes, platelets,and granulocytes was washed and resuspended in 65% Percoll$^R$ in PBS (by volume). Then 55% Percoll$^R$, 40% Percoll$^R$ and McCoy's media were layered, respectively , over the suspension and centrifuged at 3200 × g for 10 min with the brake off. The monocytes were recovered from the 40–55% Percoll$^R$ interface, diluted with media and washed.

Granulocytes:

Granulocytes were isolated from Ficoll$^R$ pellets by removing RBCs by agglutination. The Ficoll$^R$ pellet from lymphocyte isolation containing granulocytes and RBCs was suspended in McCoy's media and centrifuged at 3000 × g for 1 min and the buffy coat from the pellet removed. This process was repeated until the buffy coat was sufficiently enriched for granulocytes. The appropriate agglutinin (anti-A, -B, -AB, -O, and -H) was added and allowed to agglutinate fully. The clumps were then spun at 1500 × g for less than 1 sec and the supernatant layered over Ficoll$^R$ (1.3545 g/ml) and centrifuged at 3000 × g for 2 min. The granulocyte-enriched pellet was then washed and tested against antiblast sera. (This entire process was done in Fisher tubes using a Fisher, Model 59, centrifuge.)

Methods Used to Characterise CBL1 Reactivity

A. Cytotoxicity.

Cytotoxicity tests measure the extent of killing of a cell population by cytotoxic monoclonal antibodies. The antibody binds to the cell surface and the cell is lysed or killed by complement components in serum. ural method used by the body to kill tumor cells reactive with infused monoclonal antibodies. A rapid cytotoxic screening test was used to determine the specificity of the subject antibody for tumor cells and not normal cells. One microliter of antibody at dilutions from 1:10 to 1:10⁷ were added to 2000 viable cells in wells of a microtiter plate. Following incubation of 30 mins that allows the antibody time to bind to the cell, rabbit serum (5 ul) was added for one hour. The complement components in the rabbit serum killed cells that bound antibody but not cells that did not bind antibody. The dead cells are identified by adding a red colored dye (eosin) which enters dead cells but not living cells. The number of dead cells can be counted using a light microscope at 200× magnification. (Billing et al 1979 Immunol. Immunopathol. 13, 435).

B. Tissue Staining.

A different method of antibody binding test was used to identify the positive cells in tissue sections from patients. A thin slice (6–8 microns) of the frozen organ tissues was cut by a cryostat and placed on a microscope slide. The tissue sections were fixed in acetone for 10 mins. Dilutions of the monoclonal antibody from 1:10 to 1:10,000 were added to the slides. They were incubated for 15 mins with a second antibody, peroxidase linked goat anti-mouse immunoglobulin. Following a wash step the substrate for the peroxidase enzyme, aminoethyl carbazole (AEC), was added for 10 mins. After a final wash the tissues were counterstained with Mayer's hematoxylin and preserved in aquamount (Lerner Laboratories). The cells that contained the antigen stained a reddish brown color whereas negative cells and tissue stained pale blue due to the counterstain, Mayer hematoxylin. Control studies included staining with normal mouse ascites and a mouse monoclonal antibody against normal human leukocytes.

C. Molecular Weight of the Antigenic Determinant.

The method of Immunoprecipitation and Polyacrylamide Gel Electrophoresis was used. Cell (5×10⁶ per experiment) were labelled with ¹²⁵I by the iodogen technique of Markwell and Fox (1978) Biochemistry 17: 4807–4817, solubilised with 300 ml 0.5% Nonidet$^R$ P40, and immunoprecipitated with 10 ul CBL1 bound to 40 ul rabbit anti-mouse IgM-protein A Sepharose 4B. After washing three times with PBS, the precipitated antigens were released from the protein A by adding 50 ul 2% SDS. They were boiled for 2 mins with or without dithiothreitol and run on 12% gels. Fifty 2 mm slices from each gel were counted on a gamma counter. Standard proteins of known molecular weight were also run in order to calculate the molecular weight of the precipitated antigens. The gel system was that originally described by King and Laemmli (1971) J. Mol. Biol. 62: 467–480, and used by Billing et al. (1978) J. Natl. Cancer Inst. 61: 423–429. The molecular weight and protein standards used were lysozyme 14,400, soybean trypsin inhibitor 21,500, carbonic anhydrase 31,000, ovalbumin 45,000, bovine serum albumin 68,000, phosphorylase B 92,900, and B-galactosidase 116,500.

The molecular weight of the antigen detected by the subject antibody was estimated from a graph of the migration distances of the standards plotted against their molecular weight. Tumor cells or spent culture media were used as a source of the antigen.

SDS electrophoresis of the monoclonal antibody and immunodiffusion studies with antimouse immunoglobulin subtype antisera demonstrated that the monoclonal antibody was of the IgM subclass.

The antigen can be purified from conditioned media and NP40 cell lysates (described above) by affinity chromatography using purified antibody bound to Sepharose or latex beads (Affinity chromatography by Pharmacia). Following washing of the column with phosphate buffered saline the antigen can be eluted by chaotropic agents or glycine buffer pH 2.8.

BRIEF DESCRIPTION OF THE DRAWINGS AND TABLES

The file of this patent contains at least one drawing executed in color. Copies of this patent with color drawing (s) will be provided by the Patent and Trademark Office upon request and payment of the necessary fee.

The following Figures and Tables will provide experimental results from which the characteristics of the MA and its antigen were determined. They will also give additional evidence of the uses of the invention described in the specification.

Table 1 shows the types of cells that react with the MA by cytotoxicity testing.

Table 2 gives the percentages of lymphocytes that express the CAGF antigenic determinant before and after stimulation with a mitogen PHA.

Table 3 shows growth study results with CBL1.

Table 4 shows allogeneic skin graft survival times in Rhesus monkeys treated with the MA, CBL1.

The description of the invention will be expanded below.

A. Characterisation of the CBL1 Reactivity

Table 1 shows the results of testing the MA for killing of human cell types. The cells that were highly positive were cultured solid tumor cells, leukemia cells, activated lymphocytes and monocytes. Most normal non-dividing tissue cells were not reactive. Therefore the invention antibody is reactive with an antigen that is present essentially on cells that are dividing. Activated lymphocytes are dividing under normal immunological conditions in that they have been stimulated to divide as part of the normal immune response to a foreign antigen. Cancer cells are dividing uncontrollably.

TABLE 1

MONOCLONAL ANTIBODY REACTIONS AGAINST NORMAL AND MALIGNANT CELLS

| | # of samples | % positive |
|---|---|---|
| Normal cells - Type | | |
| Peripheral blood T cells | 12 | <2% |
| Peripheral blood B cells | 12 | <2% |
| Peripheral blood granulocytes | 12 | <2% |
| Peripheral blood platelets | 10 | <2% |
| Peripheral blood monocutes | 15 | >80% |
| Peripheral blood activated lymphocytes | 6 | >60% |

TABLE 1-continued

MONOCLONAL ANTIBODY REACTIONS AGAINST NORMAL AND MALIGNANT CELLS

| | # of samples | % positive |
|---|---|---|
| Malignant cells - Type | | |
| Acute myeloid leukemias | 25 | >95% |
| Acute lymphoid leukemias | 28 | >95% |
| Chronic myeloid blast crisis | 10 | >95% |
| Chronic lymphocytic leukemias | 20 | <2% |
| Cultured leukemia cell lines, Reh, CEM, HSB2, Daudi, Raji, HL60, KG, JM, Molt 4, BJAB | 10 | >95% |
| Tumor cell lines ( ) is number of different cell lines tested, colorectal (3), lung (4), liver (1), breast (2), prostate (1), kidney (1), exophagus (2), bladder (2). | 16 | >95% |
| Tumor cells in frozen tissue sections ( ) is number of different carcinomas tested, colon (6), rectal (1), esophageal (2), breast (5), kidney (1), meningioma (3), pancreatic (1), adrenal (1). | 20 | + ve by immunoperoxidase staining |

The photographs (FIGS. 1–4) show tissue sections of colon and breast cancer tissue stained with CBL1 and goat anti-mouse immunoglobulin bound to peroxidase. The substrate is aminoethyl carbazole (AEC) which gives a positive reddish-brown stain. The tissues are counter-stained with Mayer hematoxylin which shows a background intensity of blue proportional to the cell density. The photographs demonstrate the specificity of CBL1 for tumor tissue.

FIG. 1 shows colon carcinoma stained with CBL1. Magnification is 250x. The malignant tissue that is present on the left side of the photograph is stained reddish-brown showing reaction with CBL1, whereas the normal colon endothelium on the right is negative. The large blue mass at the top right of center is a lymph node showing no reaction with CBL1.

Figure 2:
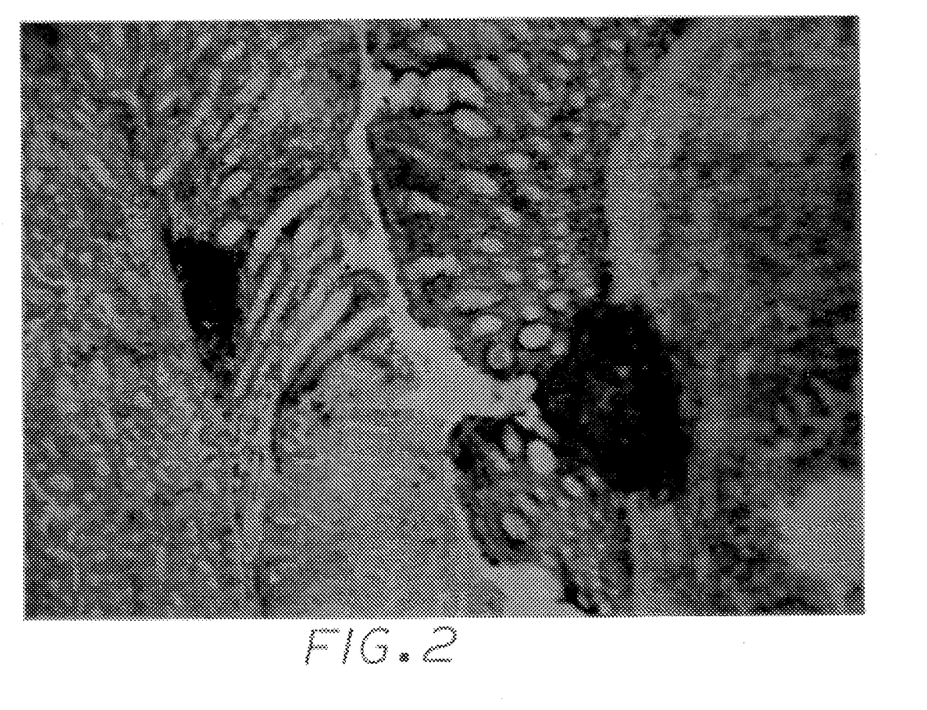

FIG. 2 shows the same colon carcinoma section stained with mouse monoclonal antibody against normal or human lymphocyte antigen (T29). Magnification 250x. This is a negative control for the CBL1. T29 does not stain the tumor tissue on the left but stains lymphoid cell infiltrates in the endothelium on the right and the normal lymph node (lower right).

Figure 3:
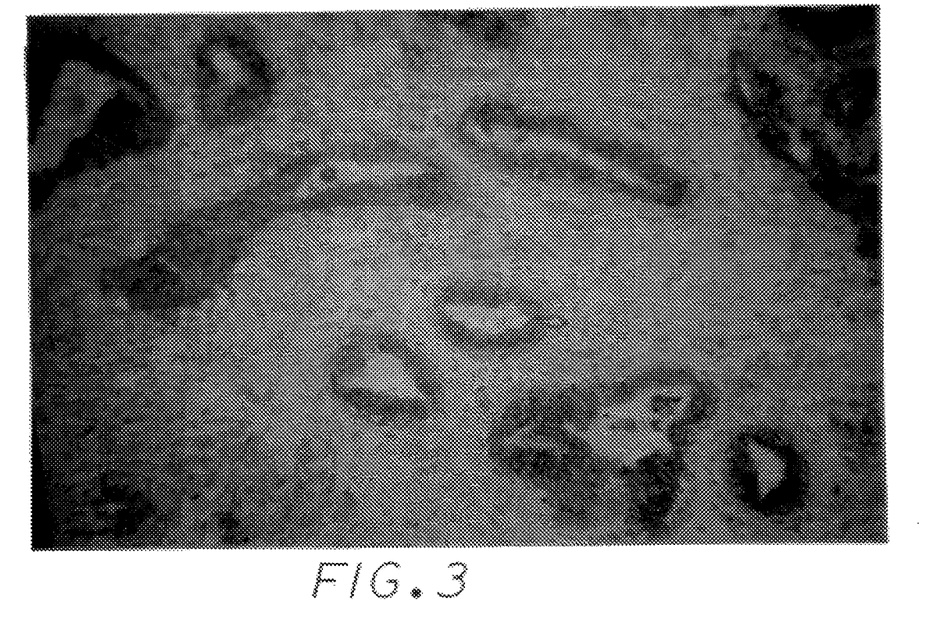

FIG. 3 shows breast cancer tissue stained with CBL1. Magnification 100x. The malignant cells surrounding the glandular ducts are CBL1 positive whereas the normal stroma is CBL1 negative.

Figure 4:
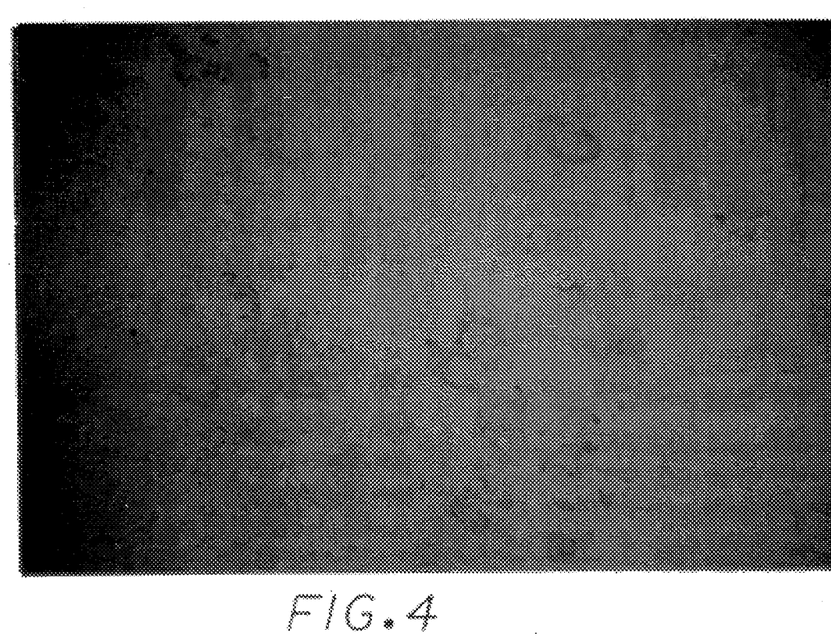

FIG. 4 shows normal breast tissue stained with CBL1. Magnification 100x. There are no CBL1 stained cells.

In addition to the tissues shown in the photographs, the following different carcinomas were stained positive for CBL1. The number in parenthesis represents the number of patients tested:- colon (6), rectal (1), esophageal (2), breast (5), kidney (1), meningioma (3), pancreatic (1), adrenal (1). Normal tissue from healthy donors and normal tissue adajcent to malignant tissue was not stained and therefore unreactive with CBL1.

B. Presence of Antigenic Determinant on Activated Lymphocytes

Table 2 illustrates by immunoperoxidase staining of lymphocytes with the CBL1 antibody that the CBL1 antigen is present in the cytoplasm of unstimulated normal lymphocytes. It is not present on the cell surface of these cells. Five hours following stimulation of the lymphocytes with PHA or allogeneic lymphocytes, the CBL1 antigen is present on the cell surface membrane in addition to also being in the cytoplasm. Therefore the antigen must have some function at the cell membrane of activated or dividing cells. This function as described below appears to be that of a growth promoting agent or growth factor. As a control, the OKT9 antibody that reacts with blast cells was present only on the surface of activated cells. The CBL1 antigen is unique in that it is found in the cytoplasm but not the cell surface of non-dividing lymphocytes and it is present on the cell surface of dividing cells such as activated lymphocytes and cancer cells.

TABLE 2

PERCENT POSITIVE CELLS IN CULTURE OF PHA STIMULATED VERSUS UNSTIMULATED PERIPHERAL BLOOD LYMPHOCYTES

| ANTIBODY | PERCENTAGE CELLS WITH POSITIVE SURFACE STAINING | | PERCENTAGE CELLS WITH POSITIVE CYTOPLASTIC STAINING | |
|---|---|---|---|---|
| | PHA | NO PHA | PHA | NO PHA |
| A. CBL1 (a)* | 44 | 0 | 97 | 97 |
| CBL1 (b) | 21 | 11 | 97 | 96 |
| CBL1 (c) | 20 | 3 | 91 | 92 |
| B. OKT9 (c) | 22 | 3 | 33 | <1 |
| OKT9 (d) | n.d. | n.d. | 30 | 5 |

*Lower case letters identify the individual PBL donors.

C. Growth factor studies

The CBL1 antibody inhibits the division of tumor cells growing in tissue culture by binding to a soluble antigen in the culture medium (Table 3).

Serum free conditioned media supernatant from growing tumor cells at a density of $1\times10^6$ / ml will support the growth of live tumor cells growing at a low density ($10^5$ / ml). Without 20% conditioned media supernatant these tumor cell lines will die. They appear to need a growth factor which is present in the conditioned media. This growth factor could be blocked by the addition of 10–50 micrograms / ml of pure CBL1 antibody but not by three other mouse monoclonal antibodies against lymphoid cell lines. The conditioned media growth factor could be removed and isolated from the conditioned media with CBL1 affinity coated protein A beads as described on pages 12, 13. The conditioned media growth factor and the cell surface antigen detected by the CBL1 monoclonal antibody have the same molecular weight of approximately 15,000 daltons. The cancer cell related growth factor appears to be an autocrine factor meaning that it is produced and secreted by the tumor cells themselves into the cell media and stimulates growth of other cancer cells. It can be purified from growth media by ammonium sulfate precipitation followed by gel chromatography on G50 Sephadex$^R$. Treatment of the antigen with proteolytic enzymes will destroy its activity. A similar growth factor is present in mouse ascitic fluid and it may be associated with vertebrate cancers in general.

TABLE 3

RATES OF GROWTH OF TUMOR CELLS IN SERUM FREE CULTURE MEDIA IN THE PRESENCE OF GROWTH FACTOR AND MA

| ADDITIONS TO GROWTH MEDIUM | RATE OF GROWTH[1] |
|---|---|
| None | 0 |
| 20% Growth Medium (GM)[2] | + |
| 20% GM + CBL1[3] | 0 |
| 20% GM + B5[4] | + |
| Tumor cell lysate (TCL)[5] | + |
| TM + CBL1 | 0 |
| TM + B5 | + |
| Purified CAGF[6] | + |
| Purified CAGF +CBL1 | − |

[1] 0 = no growth, + = cell density increases 2 fold each day (average)
[2] Percentage of supernatant added from cells in log phase growth in serum free medium
[3] 50 ug purified MA
[4] Control MA
[5] $10 \times 10^6$ tumor cells lysed in 1 ml PBS by rapid freezing and thawing followed by centrifugation
[6] Purified by ammonium sulfate precipitation and gel filtration D. Animal Studies Studies in animal models have shown that CBL1 is capable of prolonging skin allograft survival in Rhesus monkeys without an adverse side effect. Monkeys were 5–6 Kg and received up to 0.45 ml (5 mg) daily for 16 to 22 days of CBL1 ascites with a titer of $1:10^4$. The six monkeys treated with CBL1 had no side effects and had significant prolonged skin graft (size 4×4 cm on forearm) survival durations of 20 days over that of four untreated controls in which skin grafts survived 5 days. Differential blood counts taken every other day revealed no changes (Table 4) and all animals were healthy and well.

TABLE 4

SKIN GRAFT SURVIVAL IN RHESUS MONKEYS TREATED WITH MONOCLONAL ANTIBODY CBL1

| EXP # | ANIMAL # | TITER | DOSE/ LAMDA | SKIN GRAFT SURVIVAL |
|---|---|---|---|---|
| 1 | 17182 | $10^4$ | 300 | 16 days |
| 2 | 17083 | $10^4$ | 300 | 16 days |
| 3 | 17085 | $10^4$ | 300 | 15 days |
| 4 | 7633 | $10^4$ | 450 | 22 days |
| 5 | 7212 | $10^4$ | 450 | 20 days |
| 6 | 7253 | $10^4$ | 450 | 20 days |

E. Human Studies

Figure 5:
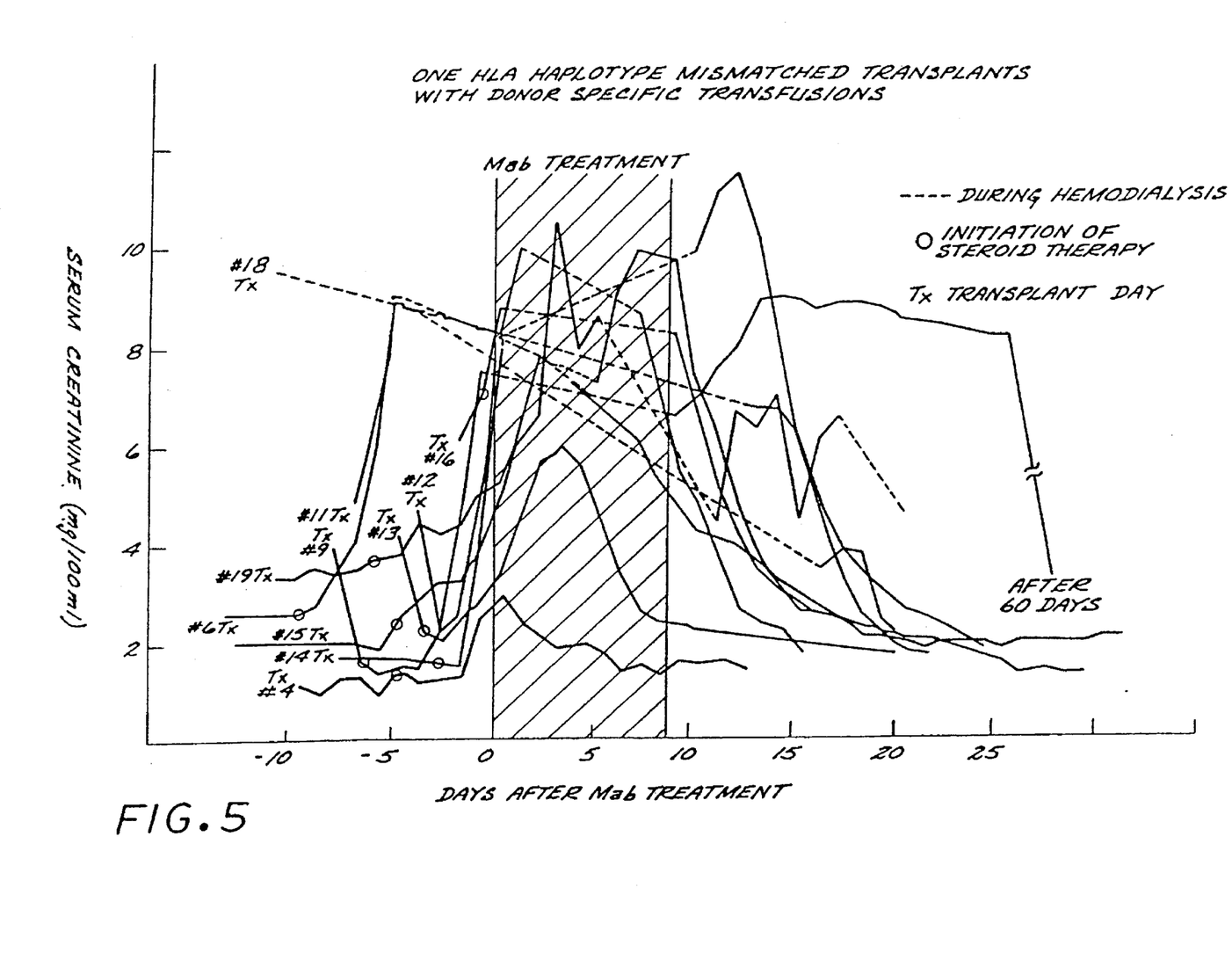
FIGS. 5–7 shows rejection course monitored by serum creatinine of kidney transplants.
Figure 6:
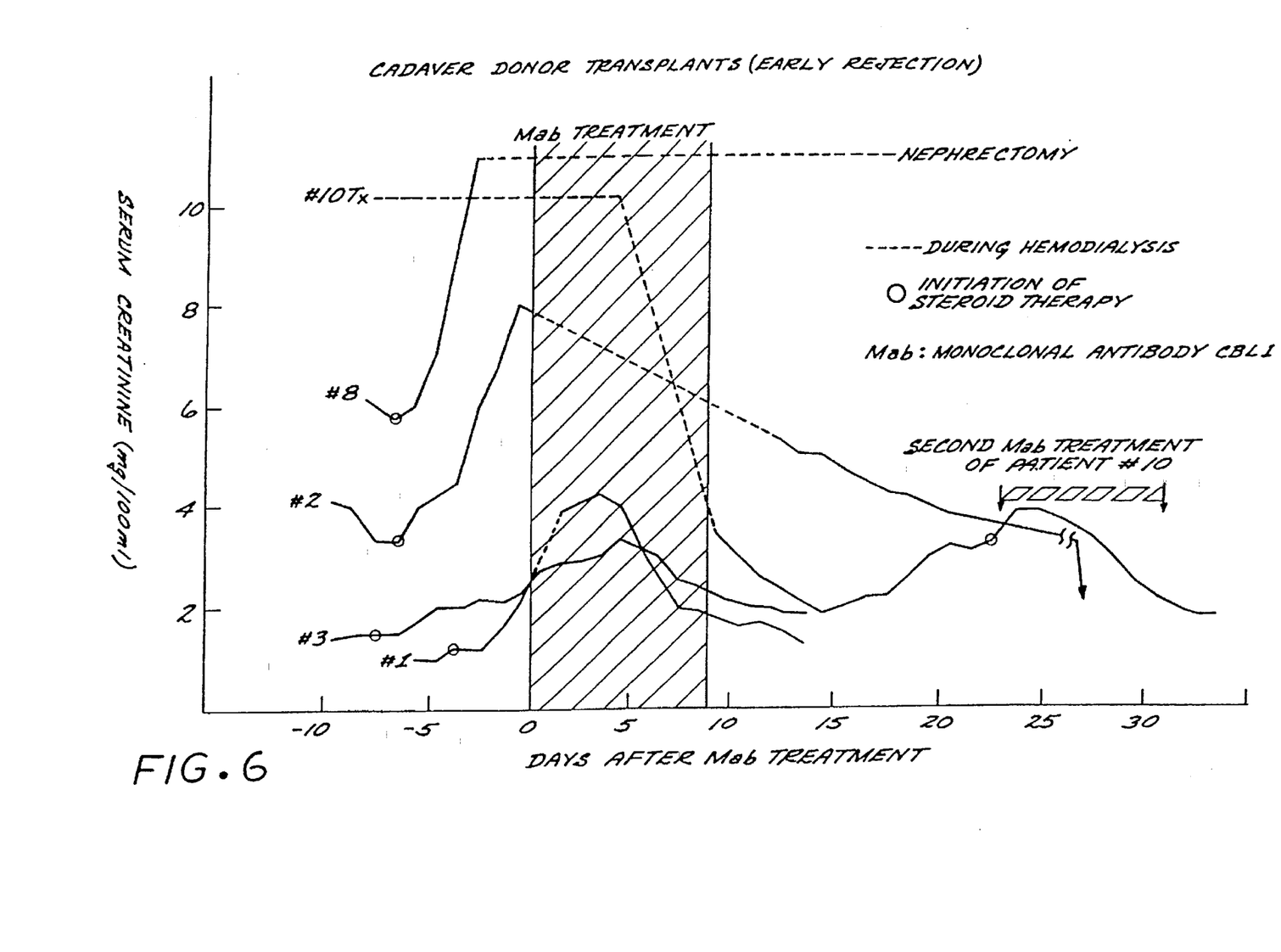
Figure 7:
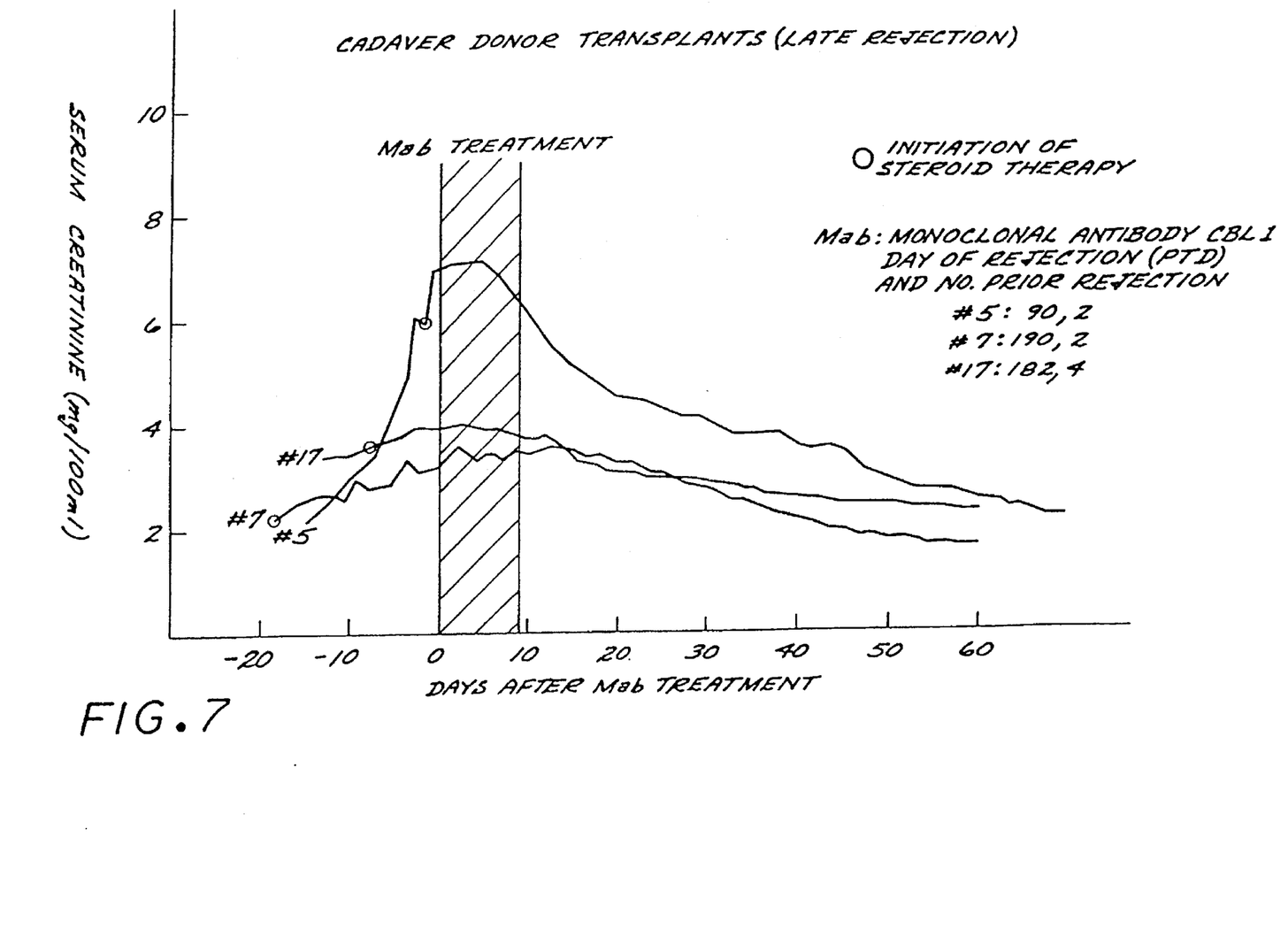
Figure 8:
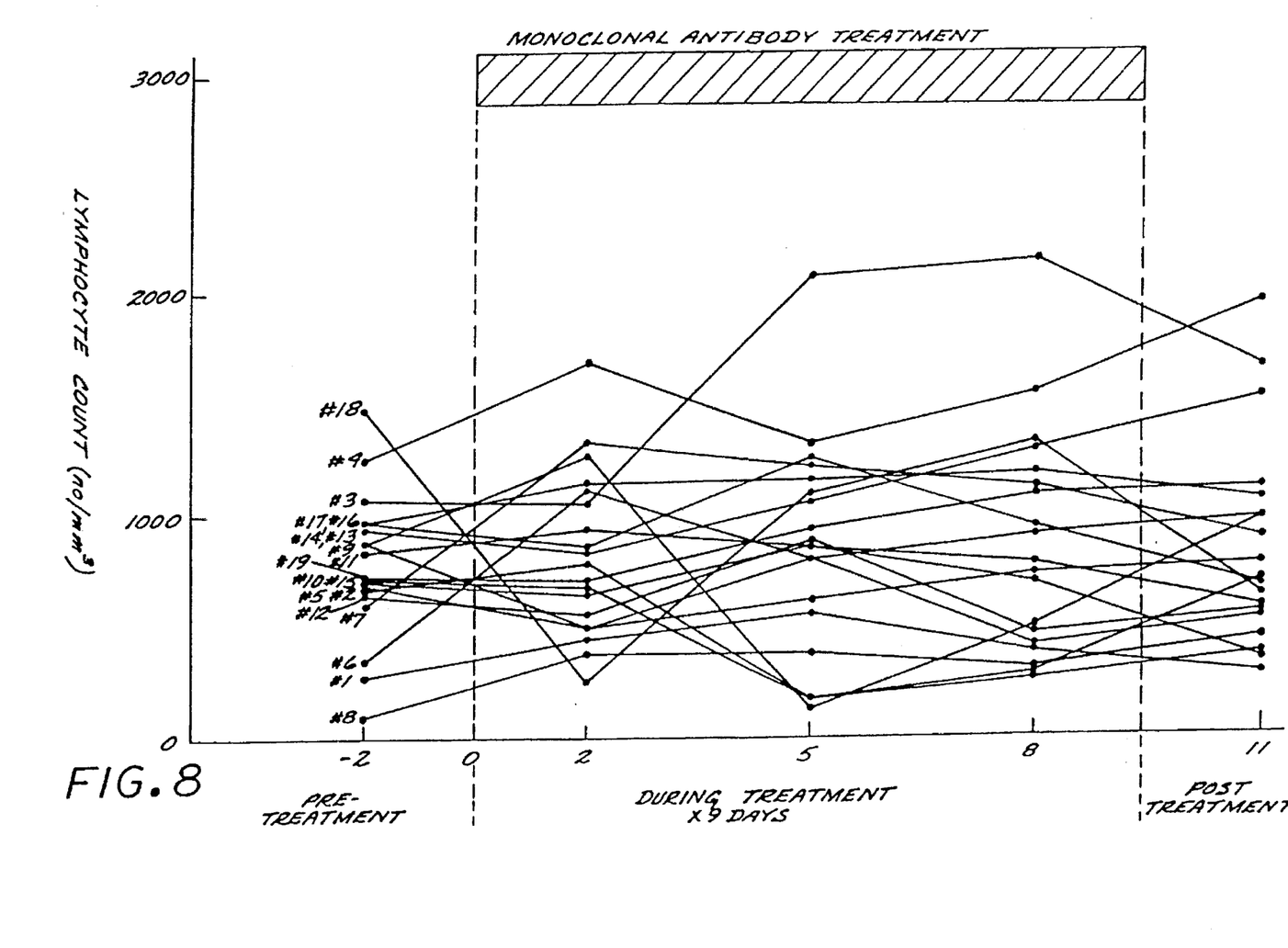
FIG. 8 shows the monitoring of blood lymphocyte counts during MA treatment.

Nineteen patients with severe steroid resistant kidney graft rejections were treated with the monoclonal antibody. Five mg in 200 ml of saline was given intravenously on 9 successive days. None of the 19 patients developed fever, vomiting, treatment created infections or other side effects. All patients had previously been immunosuppressed with conventional antirejection steroid drugs which had lowered blood counts and failed to reverse transplant rejection. There was a dramatic reversal of graft rejection in 17 cases. The creatinine clearance which was dangerously high indicating kidney rejection (greater than 4 mg/dL) showed a rapid decrease to normal levels starting on average 6 days following treatment, (FIGS. 5–7). With CBL1 treatment there was no fall in peripheral blood lymphocytes (FIG. 8), thrombocytopenia, and no reduction in peripheral blood monocyte count. Recurrence of graft rejection was uncommon after CBL1. One patient (#10, FIG. 6) who had a recurrence of graft rejection 8 months after received a 2nd treatment with CBL1 that again reversed rejection. Apart from this case the majority of the treated patients have had functioning kidneys for more than 2 years. No other antibody or medication described in prior art has been able to reverse acute rejection without frequent reoccurrences of rejection.

A similar clinical study was done on three kidney transplant patients and six corneal graft patients at UCSD. Again conventional steroid rejection therapy had failed. Following i.v. CBL1 treatment with ascitic fluid dramatic reversal of graft rejection was seen in all cases without side effects. The dose of CBL1 ascites was 0.5 ml daily for 9 days in 100–200 ml of saline administered intravenously. The titer was $1:10^4$ to $1:10^5$. Blood counts and vital signs showed no adverse effects during or after treatment. In the case of the corneal graft rejection the patient's vision was very limited due to opaqueness caused by rejection. Following CBL1 therapy normal vision was restored in all cases.

Four patients with advanced metastatic cancer have been treated with CBL1, 5 mg per day for 10 days i.v. Tumor size was reduced following the treatment and no adverse side effects were noted. These studies are in their preliminary stages.

Case 1.

Figure 9:
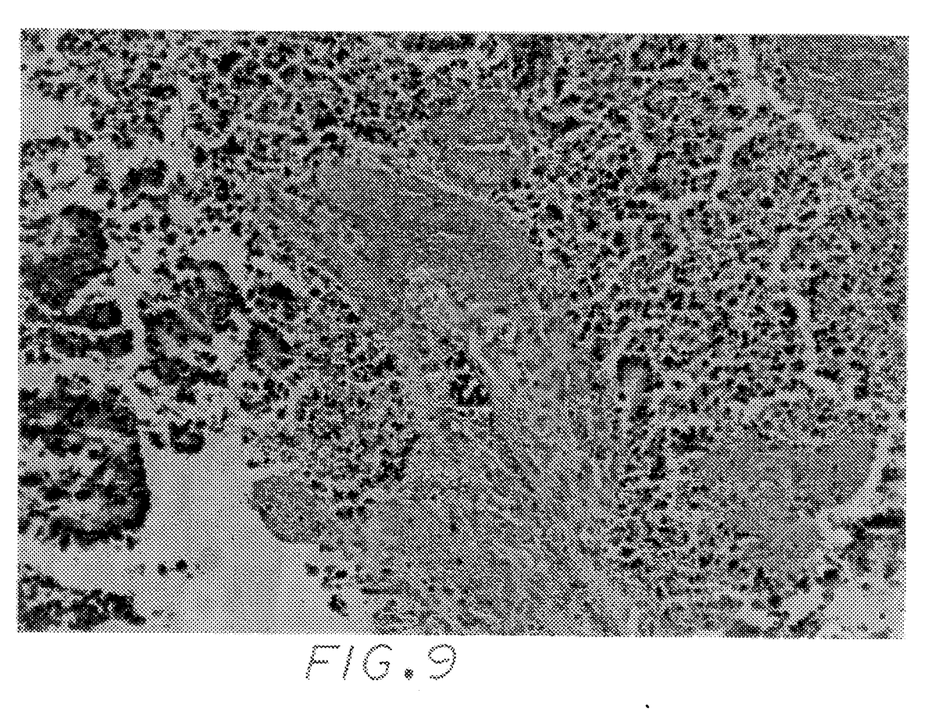
FIG. 9 shows a stained skin section containing areas of necrotic tissue. The patient (EC) was treated with MA.

A 66 year old male (EC) with metastatic colon cancer in the lymph nodes, spleen, abdomen and liver 3 years following surgery had developed an ulcer following extensive chemotherapy and was hospitalised for intravenous feeding. Following intravenously 0.5 ml CBL1 ascites daily for 10 days a large palpable abdominal tumor became necrotic and the skin lesion healed. Several weeks later he died of malnutrition while still on intravenous feeding. Tissue sections taken from autopsy tissue showed extensive necrosis of tumor cells but no visible damage to normal tissue. FIG. 9 shows necrosis of malignant skin.

Case 2.

A 48 year old male (GL) with a 2 cm diameter squamous cell carcinoma in the nasopharyngeal area received six 0.5 cc doses of CBL1 ascites intramuscularly. One week following the treatment the tumor was no longer visible by endoscopy. Four weeks later s scan by magnetic resonance imaging revealed no evidence of the tumor in the nasopharynx. No evidence of side effects were observed.

Case 3.

A male (JB) with colorectal cancer with metastasis to the lymph nodes and lower abdomen causing a large tumor abscess on the left groin and protruding rectal tumor was treated with CBL1 purified monoclonal antibody. Following ten daily treatments of 20 mg per day the tumor abscess healed completely and the protruding rectal tumor receded.

Case 4.

A 58 year old male (JR) diagnosed as primary Dukes C colon cancer had lymph node and liver metastasis following surgical removal of the tumor in the colon. His CEA level following surgery was 16 ng/ml which indicated a poor prognosis. Following 5 months of chemotherapy his condition had not changed. 22 months following i.m. CBL1 treatment the lymph node metastasis receded and he is still alive and well with a single metastatic tumor in the liver.

What is claimed:

1. An IgM antibody recognizing the epitope recognized by the CBL1 monoclonal antibody secreted by the hybridoma having accession no. ATCC #HB 8214.

* * * * *